United States Patent [19]

Yaginuma et al.

[11] Patent Number: 4,801,697
[45] Date of Patent: Jan. 31, 1989

[54] PHYSIOLOGICALLY ACTIVE SUBSTANCE TPI AND PRODUCTION THEREOF

[75] Inventors: Satoshi Yaginuma; Masashi Awata; Masaki Takada; Kenji Kinoshita, all of Shizuoka, Japan

[73] Assignee: Toyo Jozo Kabushiki Kaisha, Shizuoka, Japan

[21] Appl. No.: 847,312

[22] Filed: Apr. 2, 1986

[30] Foreign Application Priority Data

Apr. 2, 1985 [JP] Japan .................................. 60-68409
Nov. 15, 1985 [JP] Japan ................................ 60-255978

[51] Int. Cl.$^4$ .................... C07H 15/00; A61K 31/715
[52] U.S. Cl. .................................... 536/4.1; 536/16.8; 560/106; 435/74
[58] Field of Search ................ 536/4.1, 16.8; 560/106; 435/74

[56] References Cited

U.S. PATENT DOCUMENTS

| | | | |
|---|---|---|---|
| 4,007,283 | 2/1977 | Crisan et al. | 435/911 |
| 4,190,670 | 2/1980 | Marx et al. | 514/573 |
| 4,355,103 | 10/1982 | Boguslawski et al. | 935/7 |
| 4,618,675 | 10/1986 | Lichtenthaler et al. | 536/4.1 |
| 4,622,295 | 11/1986 | Ikenaka et al. | 435/22 |
| 4,693,888 | 9/1987 | Miyahara et al. | 424/440 |
| 4,710,491 | 12/1987 | Lockhoff et al. | 536/22 |
| 4,717,714 | 1/1988 | Boeck et al. | 536/16.8 |
| 4,721,781 | 1/1988 | Rowton | 536/4.1 |
| 4,725,428 | 2/1988 | Miyahara et al. | 424/54 |

OTHER PUBLICATIONS

"Isolation and Characterization of PDE-I and II, the Inhibitors of Cyclic Adenosine-3',5'-monophosphate Phosphodiesterase" *Agric. Biol. Chem.*, Yuji Enomoto et al., 42 (7), 1978, pp. 1331-1336.

"Two New Diphenyl Ethers and a New Depside from the Lichen Micarea prasina Fr.", *Aust. J. Chem.*, John A. Elix et al., 37, 1984, pp. 2349-2364.

"Reticulol, an Inhibitor of Cyclic Adenosine 3',5'-monophosphate phosphodiesterase", *The Journal of Antibiotics*, Jul. 1975, pp. 558-560.

"Structure of CC-1065 (NSC-298223), A New Antitumor Antibiotic", *The Journal of Antibiotics*, Aug. 1980, pp. 902-903.

"Terferol, An Inhibitor of Cyclic Adenosine 3',5'-monophosphate phosphodiesterase", *The Journal of Antibiotics*, Fumio Nakagawa et al., Jan. 1984, pp. 6-12.

*Primary Examiner*—Ronald W. Griffin
*Attorney, Agent, or Firm*—Young & Thompson

[57] ABSTRACT

A compound of the formula

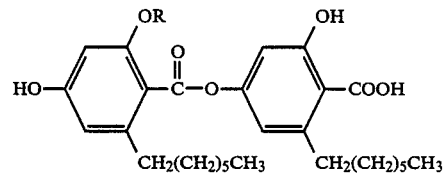

wherein R is β-D-glucopyranosyl, β-D-galactopyranosyl, 6'-O-acetyl-β-D-glucopyranosy or 6'-O-acetyl-β-D-galactopyranosyl, or a pharmaceutically acceptable salt thereof, has bronchodilator, cardiac activity, smooth muscle relaxant activity and hormone excretion stimulant activity. It can be produced by culturing a microorganism belonging to the genus Nodulisporium and adapted to produce the compound in a culture medium, and isolating the produced compound from the cultured medium. The microorganism can be Nodulisporium sp. M5220 FERM P-8133. The compounds have inhibitory activity on cyclic-adenosine-3',5'-monophosphate phosphodiesterase.

4 Claims, 10 Drawing Sheets

PHYSIOLOGICALLY ACTIVE SUBSTANCE TPI AND PRODUCTION THEREOF

This invention relates to a novel physiologically active substance TPI having inhibitory activity on cyclicadenosine-3',5'-monophosphate phosphodiesterase, and to a process for the production thereof.

Cyclic adenosine-3',5'-monophosphate (hereinafter called cyclic-AMP) has been known as an in vivo second messenger for cell membrane function, cell growth or differentiation. An enzyme which catalyzes the decomposition of c-AMP to 5'-adenosine monophosphate (hereinafter called 5'-AMP) is cyclic adenosine-3'-5'-monophosphate phosphodiesterase (hereinafter called PDE), and an inhibitor thereof can increase the level of cyclic-AMP in vivo. By this phenomenon, various effects such as bronchodilator, cardiac activity, smooth muscle relaxant activity and hormone excretion stimulant activity have been achieved.

Heretofore, among the PDE inhibitors produced by microorganisms, PDE-I or PDE-II [Agr. Biol. Chem., 42 (7), 1331-1336 (1978)], Terferol [J. Antibiotics, 37 (1), 6-9 (1984)], CC-1065 [ibid., 33 (8), 902-903 (1980)] and Reticulol [ibid., 28 (7), 558-560 (1975)] produced by Streptomyces have been known. Also substances produced by bacteria, i.e. APD-I, APD-II and APD-III [ibid., 36, 194-196 (1983)] have been known. Furthermore, synthetic chemicals which are PDE inhibitors, such as theophyllin, papaverine or nicardipine have been known. These are used as bronchodilators and vasodilators.

The search for microorganisms producing such physiologically active substances is quite important in the medical field, as is also the screening for PDE inhibitors for medical use and research study on c-AMP.

We have found, during a screening program for physiologically active substances produced by microorganisms, that a substance having inhibitory action against PDE activity was produced in a cultured broth of the genus Nodulisporium. We isolated the active principles, which were identified as novel substances and have been designated TPI-1, TPI-2, TPI-3 and TPI-4. Furthermore, we have found that a deglycosylated substance was obtained by the action of glycosidase on TPI-1, TPI-2, TPI-3 and TPI-4, and we have designated this substance TPI-5.

In this specification, TPI-1, TPI-2, TPI-3, TPI-4 and TPI-5 will be generally referred to as TPI.

An object of the present invention is accordingly to provide a novel physiologically active substance TPI of the formula $$\text{(I)}$$

wherein R is $\beta$-D-glucopyranosyl, $\beta$-D-galatopyranosyl, 6'-O-acetyl-$\beta$-D-glucopyranosyl, 6'-O-acetyl-$\beta$-D-galactopyranosyl or hydrogen, or a pharmaceutically acceptable salt thereof.

Another object of the present invention is to provide a process for the production of novel PDE inhibitors, which are TPI's having the formula (I) which comprises culturing a TPI-producing microorganism of the genus Nodulisporium, and isolating the thus-produced TPI from the cultured medium.

In the formula (I), the substituent R and name of the compound are as follows:

| Compound | R |
|---|---|
| TPI-1 | $\beta$-D-glucopyranosyl |
| TPI-2 | $\beta$-D-galactopyranosyl |
| TPI-3 | 6'-O-acetyl-$\beta$-D-glucopyranosyl |
| TPI-4 | 6'-O-acetyl-$\beta$-D-galactopyranosyl |
| TPI-5 | hydrogen |

Figure 1:
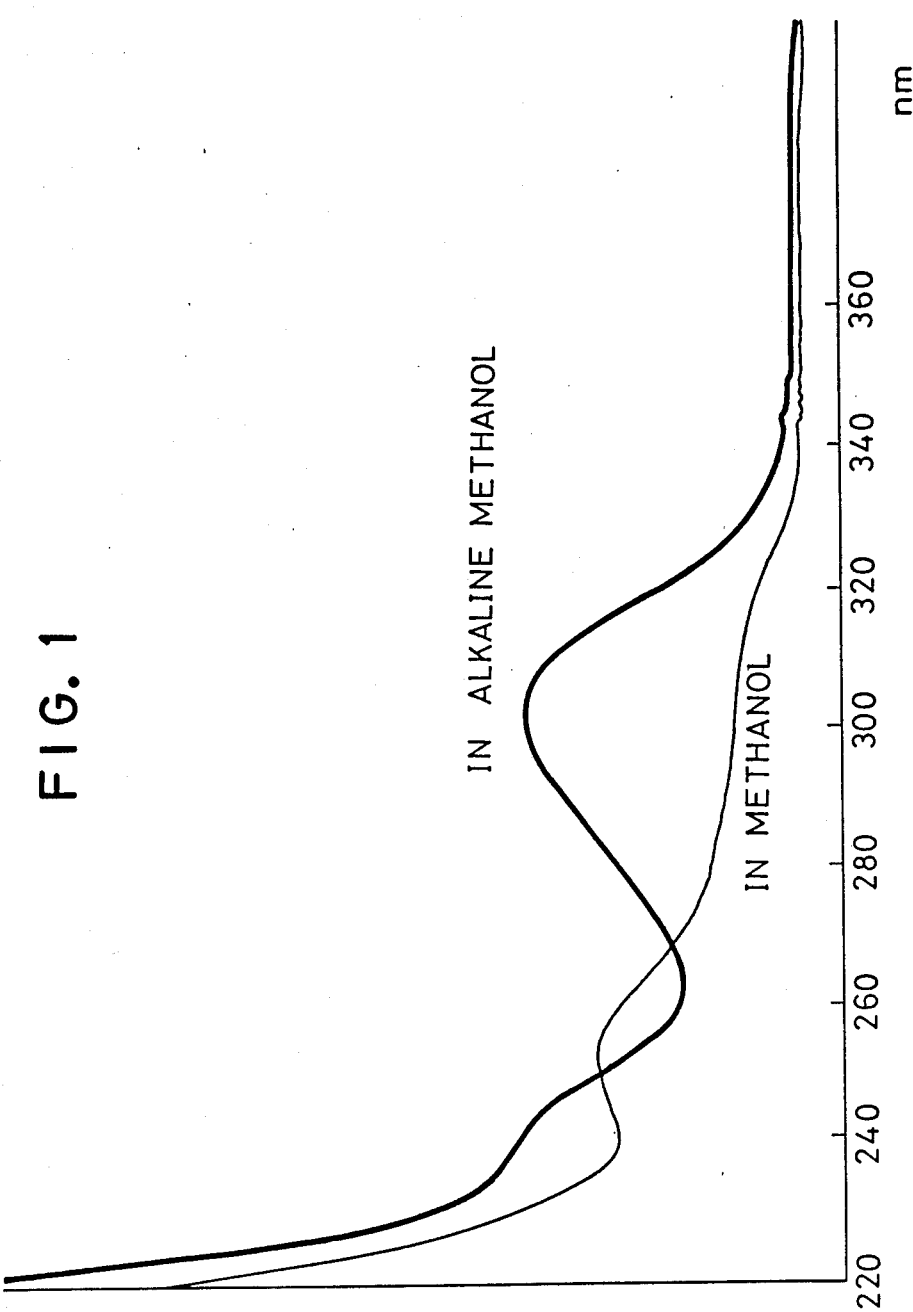
FIG. 1 is the ultraviolet absorption spectrum of TPI-1.

A microorganism strain M5220 which produces physiologically active substances TPI(II) of the formula (II)

$$\text{(II)}$$

wherein R' is $\beta$-D-glucopyranosyl, $\beta$-D-galactopyranosyl, 6'-O-acetyl-$\beta$-D-glucopyranosyl, or 6'-O-acetyl-$\beta$-D-galactopyranosyl, has the following taxonomical properties:

1. Morphological properties:

Observations on Czapeck agar medium, malt extract agar medium and potato-glucose agar medium are as follows:

Vegetative mycelia form monotrichic or synnemata, yellowish, elongate 2.5-3.0 μm width and smooth surface. Conidiophors are 50-130×2.5-3.0 μm in size, colorless to pale yellow, branched, with septa and smooth surface. Conidiogenous cells are singular or verticillate with 2-3 verticillations on a top of conidiophores, 6-20×2.0-2.5 μm in size, colorless to pale yellow. Type of conidia formation is Sympodulosporae. Formed conidia are 3.0-5.0×2.0-2.8 μm in size, unicellular and smooth surfaced.

2. Growth conditions on various media:

Observation on various media cultured at 26° C. for 10 days are as follows. Color representation conforms to A. Kornerup and J. H. Wanscher, "Methuen Handbook of Colour", 3rd Ed., Eyre Methuen, London (1978).

(1) Czapek agar medium:

Slowly grown 11–13 mm in diameter at 26° C. for 10 days culture. Colonies are flat and velvety to slightly cottony. Dark green color (30F6). Smooth edges. No exudate and diffusible pigment. Reverse side color is dark green (27F5).

(2) Malt extract agar medium:

Slowly grown 15–17 mm in diameter at 26° C. for 10 days culture. Colonies are thick and slightly cottony. Dark green color (27F3). Smooth edges. No exudate and diffusible pigment. Reverse side color is dark green (27F3).

(3) Potato-glucose agar medium:

Slowly grown 15–16 mm in diameter at 26° C. for 10 days culture. Colonies are thick and slightly cottony. Dark green color (27F3). Smooth edges. No exudate and diffusible pigment. Reverse side color is dark green (27F3).

3. Physiological properties:

Growth pH: 1–9.5
Optimum pH: 3–7
Growth temperature: 13°–40° C.
Optimum temperature: 25°–30° C.

According to the taxonomical properties hereinabove illustrated, the present strain having properties of forming conidia without gamogenesis and mycelia with septa, belongs to the genus Deuteromycotina. Furthermore, the present strain in which the type of conidia formation is sympodulosporae, the conidiophores are well branched, and the conidia forming cells are frequently verticillate, is a strain belonging to the genus Nodulisporium.

The present strain is referred to as Nodulisporium sp. M5220 and has been deposited in The Fermentation Research Institute, Agency of Industrial Science and Technology, M.I.T.I., Japan, as Deposit No. FERM P-8133.

The physiological active substance TPI(II) can be produced by culturing, for example a TPI(II)-producing microorganism belonging to the genus Nodulisporium, and isolating TPI(II) from the cultured mass.

An example of a TPI(II)-producing microorganism is the above illustrated strain Nodulisporium sp. M5220; however, any strain having TPI(II)-producing activity including natural and artificial mutants can be used in the present invention.

Culturing of the strain in the present invention can be performed by conventional means for fungal culture.

The medium for cultivation can be an assimilable carbon source, a digestible nitrogen source and if required inorganic salts and vitamins. Examples of carbon sources are saccharides such as glucose, fructose, maltose, sucrose, lactose, galactose, dextrin, starch, glycerol and sorbitol, and vegetable oils such as soybean oil, in combination or alone. Examples of nitrogen sources are peptone, yeast extract, meat extract, soybean powder, cotton seed powder, corn steep liquor, malt extract, casein, amino acids, urea, ammonium salts and nitrate salts, in combination or alone. Furthermore, if required, inorganic salts of magnesium, calcium, sodium potassium, iron ad manganese, and vitamins such as vitamin B and calcium pantothenate can be added.

The preferred culture technique is liquid shaking culture or aeration culture. The preferred pH of medium is pH 3–7 and temperature is 25°–30° C. Cultivation time in liquid media is usually 2–10 days, however maximum accumulation of TPI(II) can be reached within 5 days and cultivation is preferably terminated at this point. The conditions of cultivation, such as the composition of the medium, temperature, time, etc. can be modified according to the kind of strain and other conditions, in order to obtain maximum yield and quality. Antifoaming agents such as silicone oil, vegetable oil or surface active agents can be added if necessary.

TPI(II) is present in the cultured broth, and is preferably isolated by adding a filter-aid such as Celite, Perlite or Hyflosupercel (trade name) to the cultured broth, or by centrifugation.

The isolation of TPI(II) from the culture filtrate can be performed by extracting with a water-immiscible organic solvent such as ethyl acetate, butyl acetate or butanol and concentrating the extract to obtain crude TPI(II). Further purification can be carried out by combining adsorption chromatography using silica-gel, active alumina, active carbon or non-ionic adsorption resin, reverse phase partition chromatography using alkyl-bonded silica gel, and gel filtration using a gel-filtration carrier. For example, crude TPI(II) is adsorbed on a column of silica gel or alumina and eluted with a mixed solution such as chloroform-isopropanol-acetic acid, ethyl acetate-isopropanol-acetic acid, or ethyl acetate-methanol-acetic acid. The active fractions can be checked by silica-gel thin layer chromatography or assaying an inhibitory activity using bovine heart PDE.

By such column chromatography, each component, namely TPI-1, TPI-2, TPI-3 and TPI-4 can be isolated.

TPI-5, which is a compound of the formula (III)

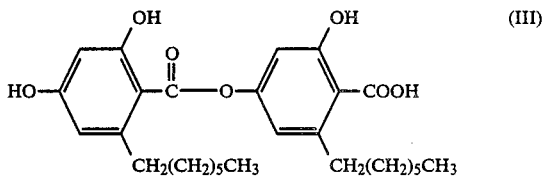

can be produced by treating TPI(II) or a salt thereof with glycosidase or its derivatives to split enzymatically the glycoside bond.

Examples of glycosidases are β-glucosidase for TPI-1 or TPI-3, and β-galactosidase for TPI-2 or TPI-4. The glycosidase can be any enzyme obtained from animal, plant or microbial origin, e.g. commercially available β-glucosidase or β-galactosidase. Microbial enzymes are exo- and endo- enzymes. Exo-enzymes can be obtained by conventional purification procedures from a culture filtrate of the enzyme-producing strain. In the case of endo-enzymes, microbial cells per se can be used. Treated microbial cells, for example dried cells prepared by dehydration with a water-immiscible organic solvent such as acetone, methanol or ethanol, ground microbial cells produced by a cell grinder or by ultrasonication, and cell lysates produced by treating with cetyl pyridinium chloride and a surface active agent, or enzymes prepared from these treated cells by conventional purification procedures, can be used in the present invention.

The modified enzyme hereinabove means a variant type of material having glycosidase activity, and immobilized enzymes or immobilized cells are also included therein.

Immobilized enzymes or cells can be prepared by conventional means. For example, a method immobilizing the enzyme with a carrier by covalent bonding, ionic bonding or adsorption, a method immobilizing the enzyme or cells by cross linkage, and an enveloping method entrapping the enzyme or cells by a semipermeable membrane for microcapsulation, empty fibers or a membrane can be mentioned. Continuous reaction can be achieved by using immobilized enzymes or cells.

The above enzymatic reaction can preferably proceed at an optimum pH. The reaction temperature should be optimum and is generally 25°-37° C. The reaction time can be determined by checking the produced TPI by thin layer chromatography (TLC) or high performance liquid chromatography (HPLC) and is preferably terminated at a maximum accumulation of TPI-5.

The thus-obtained enzymatic reaction medium is acidified, extracted with a water-immiscible organic solvent such as ethyl acetate, butyl acetate or butanol and the resulting extract is concentrated to obtain crude TPI-5 therefrom. Further purification can be achieved by chromatography, gel filtration or a like procedure the same as for TPI(II).

Salts of TPI can be conventionally prepared from crude TPI; however, salt preparation is preferably performed after purification. The preferred salts are alkali metal salts such as sodium and potassium, alkaline earth metal salts such as calcium and magnesium, aluminum and other metallic salts, ammonium salt, salts of known basic amino acids or salts of known organic amines.

The physico-chemical properties of TPI are illustrated as follows:

TPI-1

(1) Color and nature: white powder
(2) Nature: acidic substance
(3) Elementary analysis ($C_{34}H_{48}O_{12} \cdot 3/2\ H_2O$):

|  | C | H |
|---|---|---|
| found: | 60.43% | 7.48% |
| calculated: | 60.44% | 7.56% |

Figure 2:
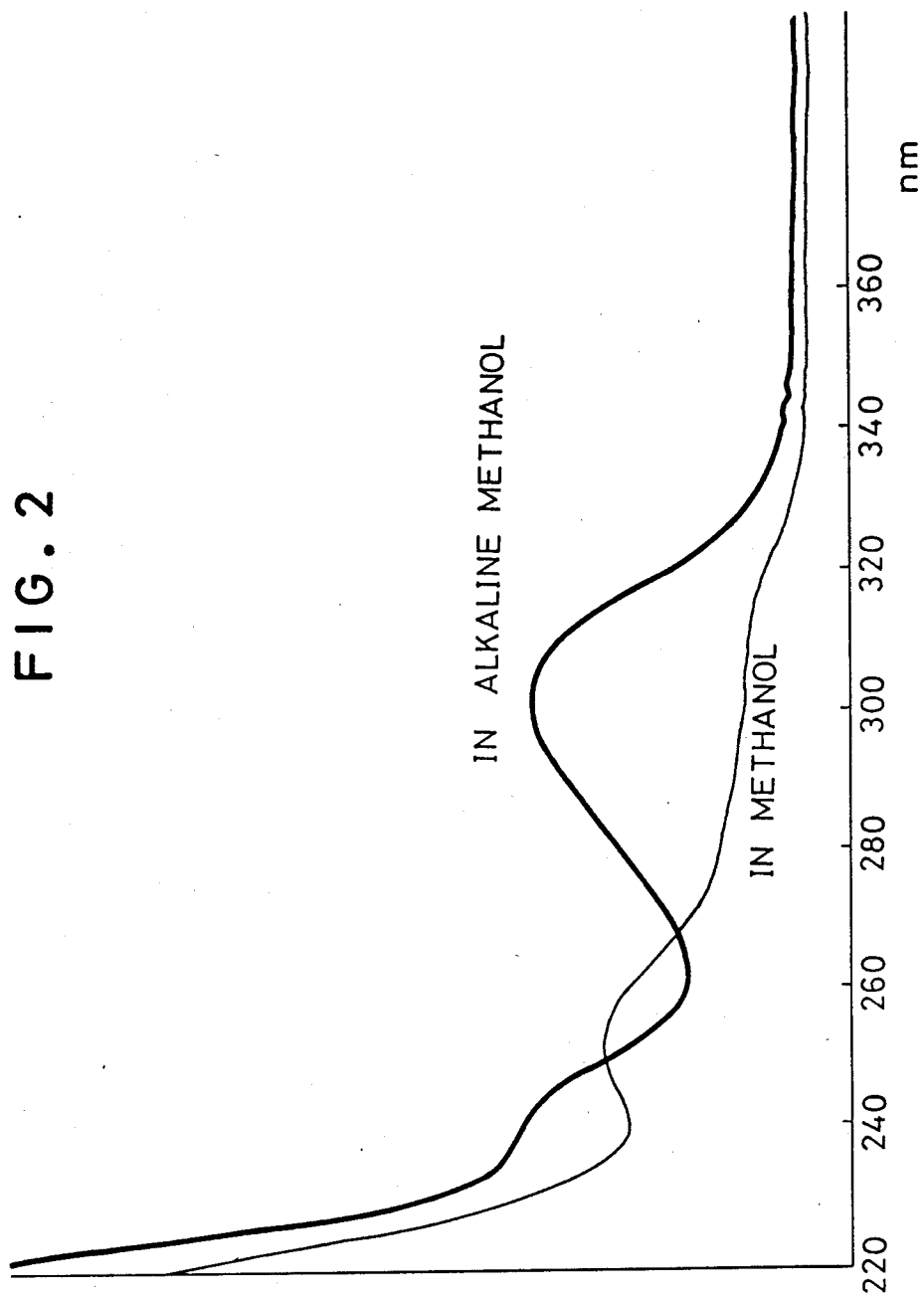
FIG. 2 is the ultraviolet absorption spectrum of TPI-2.

(4) Molecular formula: $C_{34}H_{48}O_{12}$
(5) Molecular weight (FAB mass spectrum): 648
(6) Specific rotation:
$[\alpha]_D^{25} -20.6°$ (c=1.0, MeOH)
(7) Ultraviolet absorption spectrum: (FIG. 1)
in MeOH or acidic MeOH;
$\lambda_{max}$ (nm): 253 ($E^{1\%}250$), 311 (shoulder)
in alkaline MeOH:
$\lambda_{max}$ (nm): 240 (shoulder), 300 ($E^{1\%}350$)
(8) Infrared absorption spectrum: (KBr) (FIG. 2) 3400, 2930, 2850, 1720, 1590, 1470, 1430, 1370, 1340, 1250, 1170, 1140, 1060 cm$^{-1}$.
(9) $^1$H-NMR spectrum (in deuterium methanol, 100 MHz):
δ(ppm): 0.88(t, 3H), 0.90(t, 3H), 1.31(m, 20H), 1.61(m, 4H), 2.68(t, 2H) 2.94(t, 2H), 3.40-4.00(5H), 4.89(d, 1H), 6.42(d, 1H), 6.61(d, d, 2H), 6.71(d, 1H).
(10) $^{13}$C-NMR spectrum (in deuterium methanol, 25 MHz): 174.1(s), 168.2(s), 164.2(s), 161.8(s), 158.4(s), 156.0(s), 149.1(s), 145.2(s), 116.5(d), 116.1(s), 113.5(s), 112.1(d), 109.3(d), 103.4(d), 102.7(d), 78.6(d), 78.4(d), 75.3(d), 71.6(d), 63.0(t), 37.2(t), 35.2(t), 33.3(t), 33.3(t), 33.3(t), 33.0(t), 31.1(t), 30.9(t), 30.6(t), 30.6(t), 24.0(t), 24.0(t), 14.8(q), 14.8(q).
(11) Solubility:
Soluble; lower alcohol such as methanol, ethanol and butanol, ethyl acetate, dimethylsulfoxide, aqueous alkali.
Insoluble; hexane, benzene and petroleum ether.
(12) Color reaction:
Positive; potassium permanganate reaction, ferric chloride reaction, iodine reaction and Molisch reaction
Negative; ninhydrine reaction and iodoform reaction
(13) Thin layer chromatography: (Tokyo Kasei K.K. silica-gel f)

| (Developer) | (Rf) |
|---|---|
| chloroform - isopropanol - acetic acid: (10:4:0.1) | 0.25 |
| ethyl acetate - isopropanol - acetic acid: (10:4:0.1) | 0.36 |
| ethyl acetate - acetone - acetic acid: (6:6:0.1) | 0.17 |
| chloroform - methanol - acetic acid: (10:2:0.1) | 0.38 |

TPI-2

(1) Color and nature: white powder
(2) Nature: acidic substance
(3) Elementary analysis ($C_{34}H_{48}O_{12} \cdot H_2O$):

|  | C | H |
|---|---|---|
| found: | 61.79% | 7.56% |
| calculated: | 61.26% | 7.51% |

Figure 3:
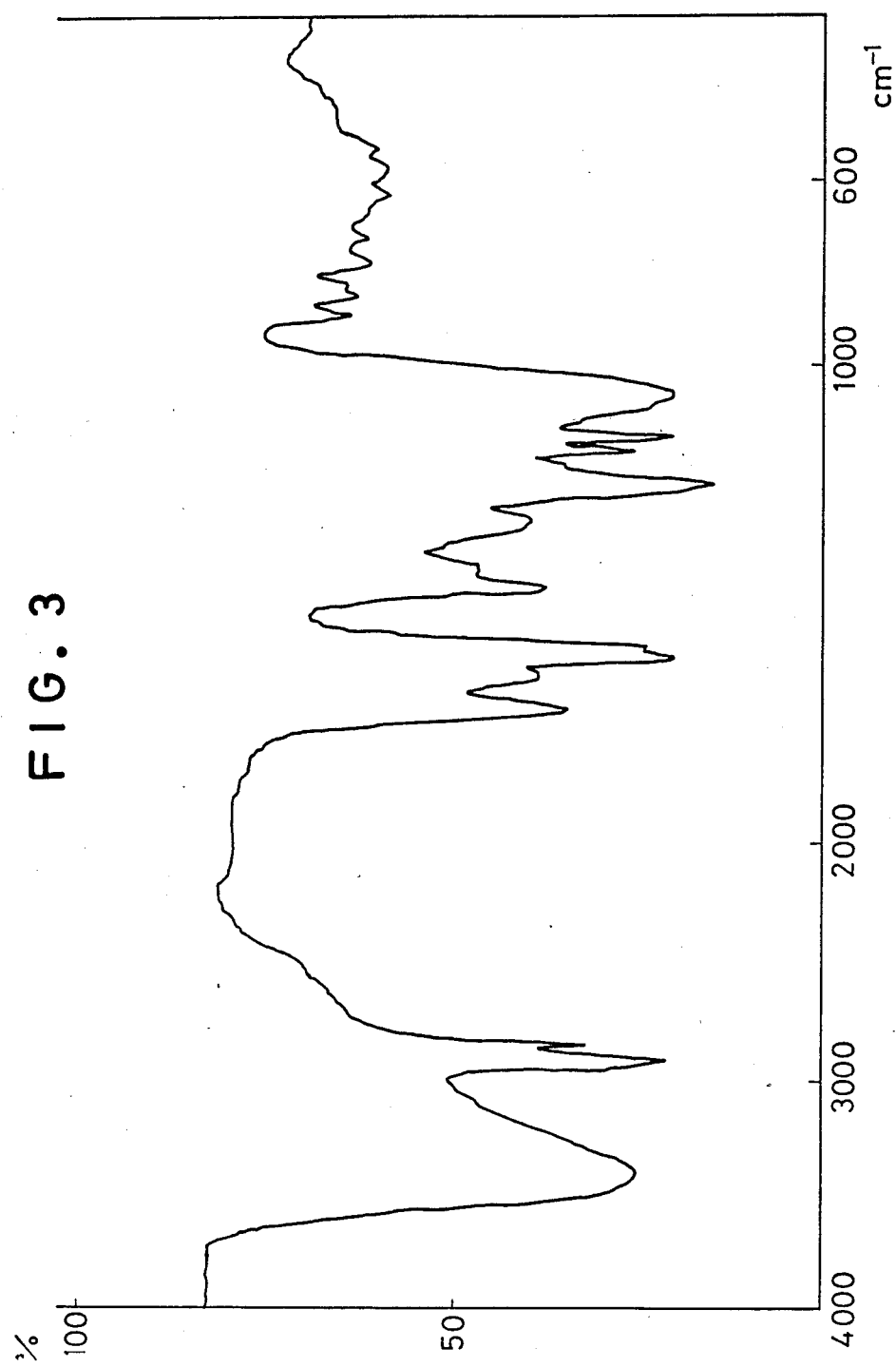
FIG. 3 is the infrared absorption spectrum of TPI-1.
Figure 4:
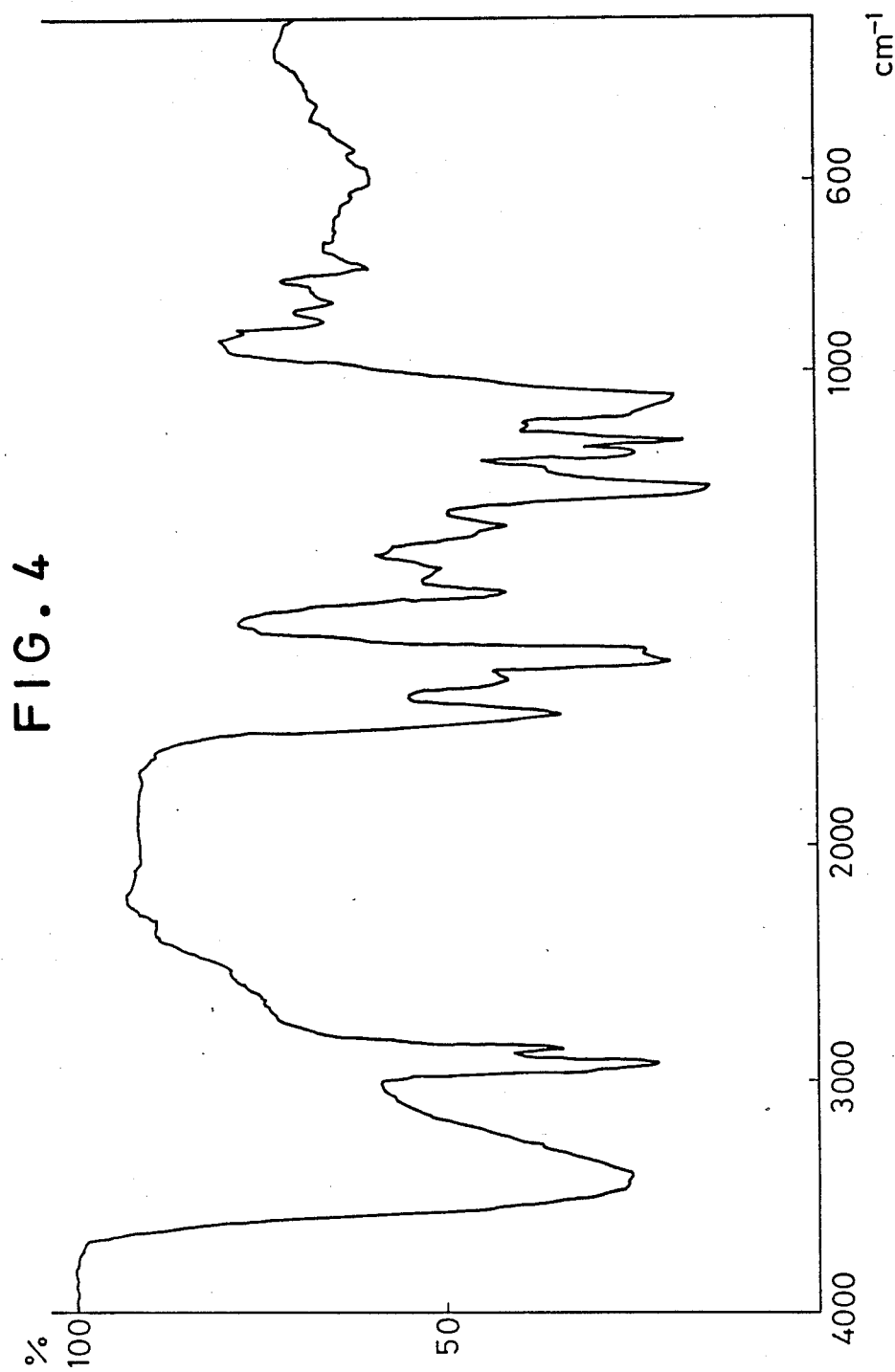
FIG. 4 is the infrared absorption spectrum of TPI-2.

(4) Molecular formula: $C_{34}H_{48}O_{12}$
(5) Molecular weight (FAB mass spectrum): 648
(6) Specific rotation:
$[\alpha]_D^{25} -12.6°$ (c=0.9, MeOH)
(7) Ultraviolet absorption spectrum: (FIG. 3)
in MeOH or acidic MeOH;
$\lambda_{max}$ (nm): 253 ($E^{1\%}230$), 311 (shoulder)
in alkaline MeOH:
$\lambda_{max}$ (nm): 240 (shoulder), 300 ($E^{1\%}325$)
(8) Infrared absorption spectrum: (KBr) (FIG. 4) 3400, 2930, 2850, 1720, 1600, 1470, 1410, 1320, 1240, 1170, 1140, 1050 cm$^{-1}$.
(9) $^1$H-NMR spectrum (in deuterium methanol, 100 MHz):
δ(ppm): 0.87(t, 3H), 0.89(t, 3H), 1.31(m, 20H), 1.60(m, 4H), 2.68(t, 2H) 2.94(t, 2H), 3.50-4.00(5H), 4.88(d, 1H), 6.42(d, 1H), 6.64(d, d, 2H), 6.74(d, 1H).
(10) $^{13}$C-NMR spectrum (in deuterium methanol, 25 MHz): 174.1(t), 168.2(s), 164.2(s), 161.8(s), 158.4(s), 156.0(s), 149.1(s), 145.2(s), 116.5(d), 116.1(s), 113.4(s), 112.1(d), 109.4(d), 104.1(d), 102.8(d), 77.4(d), 75.3(d), 72.7(d), 70.5(d), 62.7(t), 37.2(t), 35.2(t), 33.3(t), 33.3(t), 33.3(t), 33.0(t), 31.1(t), 31.0(t), 30.6(t), 30.6(t), 24.0(t), 24.0(t), 14.8(q), 14.8(q).
(11) Solubility:
Soluble; lower alcohol such as methanol, ethanol and butanol, ethyl acetate, dimethylsulfoxide, aqueous alkali.
Insoluble; hexane, benzene and petroleum ether.
(12) Color reaction:
Positive; potassium permanganate reaction, ferric chloride reaction, iodine reaction and Molisch reaction
Negative; ninhydrine reaction and iodoform reaction
(13) Thin layer chromatography: (Tokyo Kasei K.K. silica-gel f)

| (Developer) | (Rf) |
|---|---|
| chloroform - isopropanol - acetic acid: | 0.19 |

-continued

| (Developer) | (Rf) |
|---|---|
| (10:4:0.1) | |
| ethyl acetate - isopropanol - acetic acid: (10:4:0.1) | 0.21 |
| ethyl acetate - acetone - acetic acid: (6:6:0.1) | 0.14 |
| chloroform - methanol - acetic acid: (10:2:0.1) | 0.22 |

TPI-3
(1) Color and nature: white powder
(2) Nature: acidic substance
(3) Elementary analysis:

|  | C | H |
|---|---|---|
| found: | 61.93% | 7.36% |
| calculated: | 62.59% | 7.30% |

Figure 5:
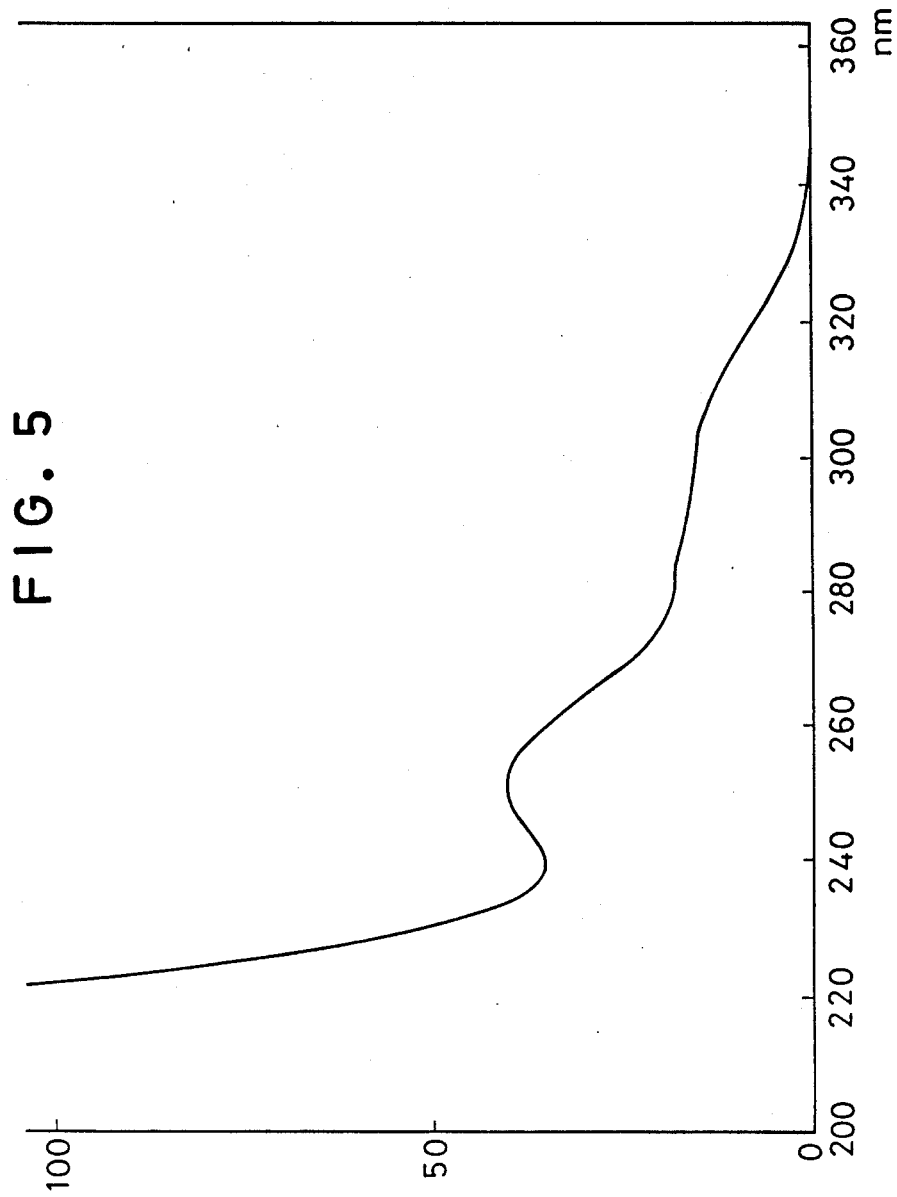
FIG. 5 is the ultraviolet absorption spectrum of TPI-3.
Figure 8:
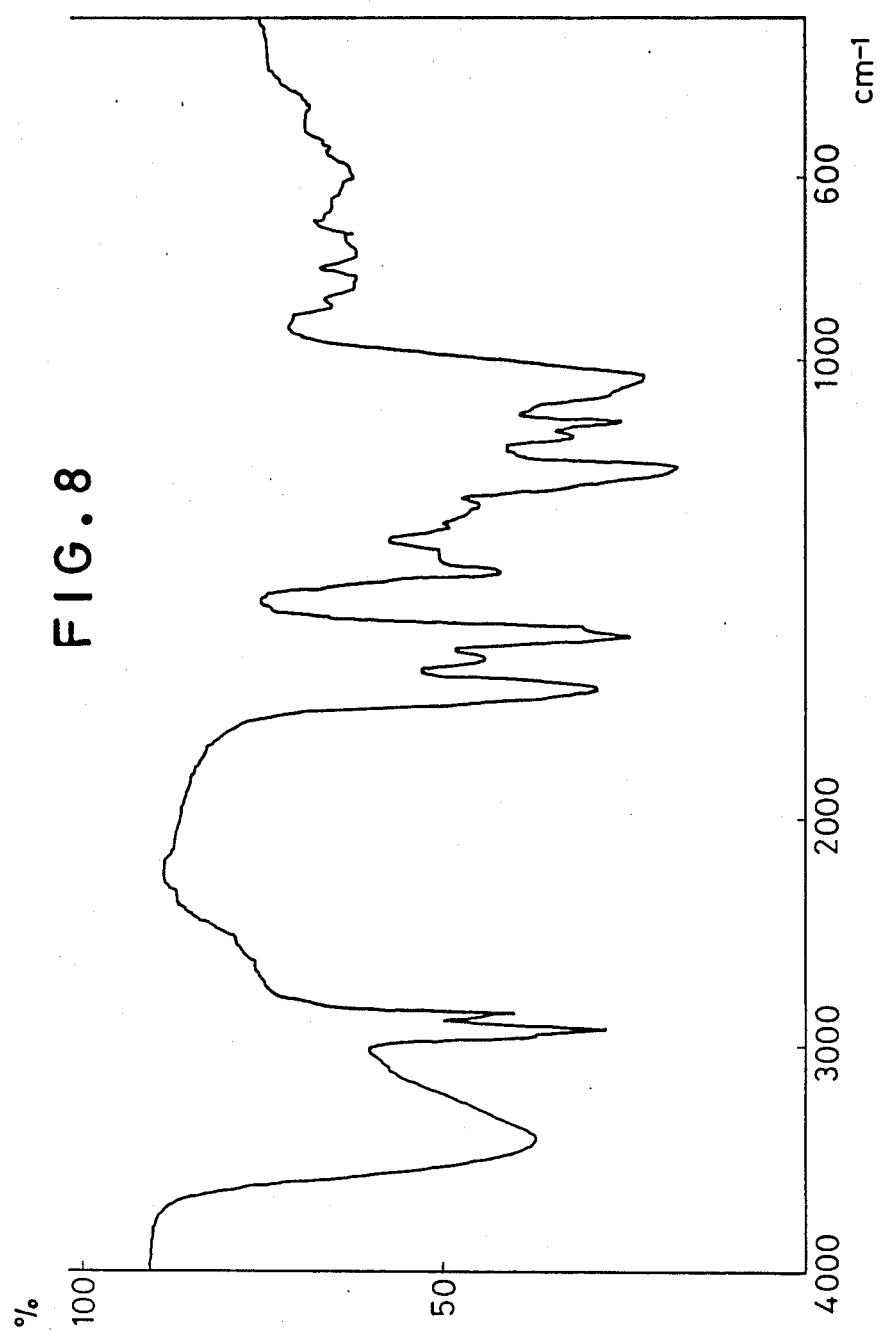
FIG. 8 is the infrared absorption spectrum of TPI-3.
Figure 9:
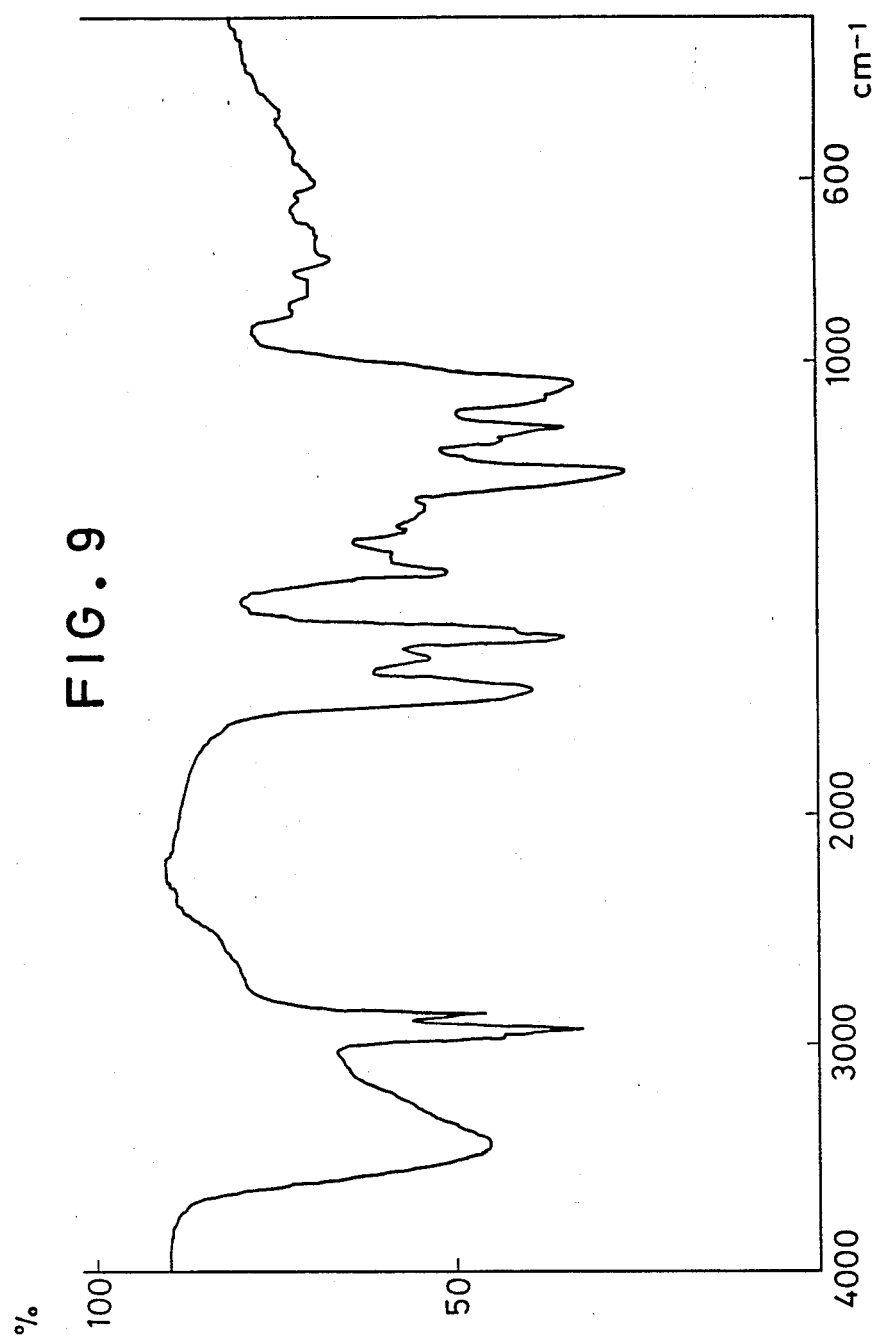
FIG. 9 is the infrared absorption spectrum of TPI-4.
Figure 10:
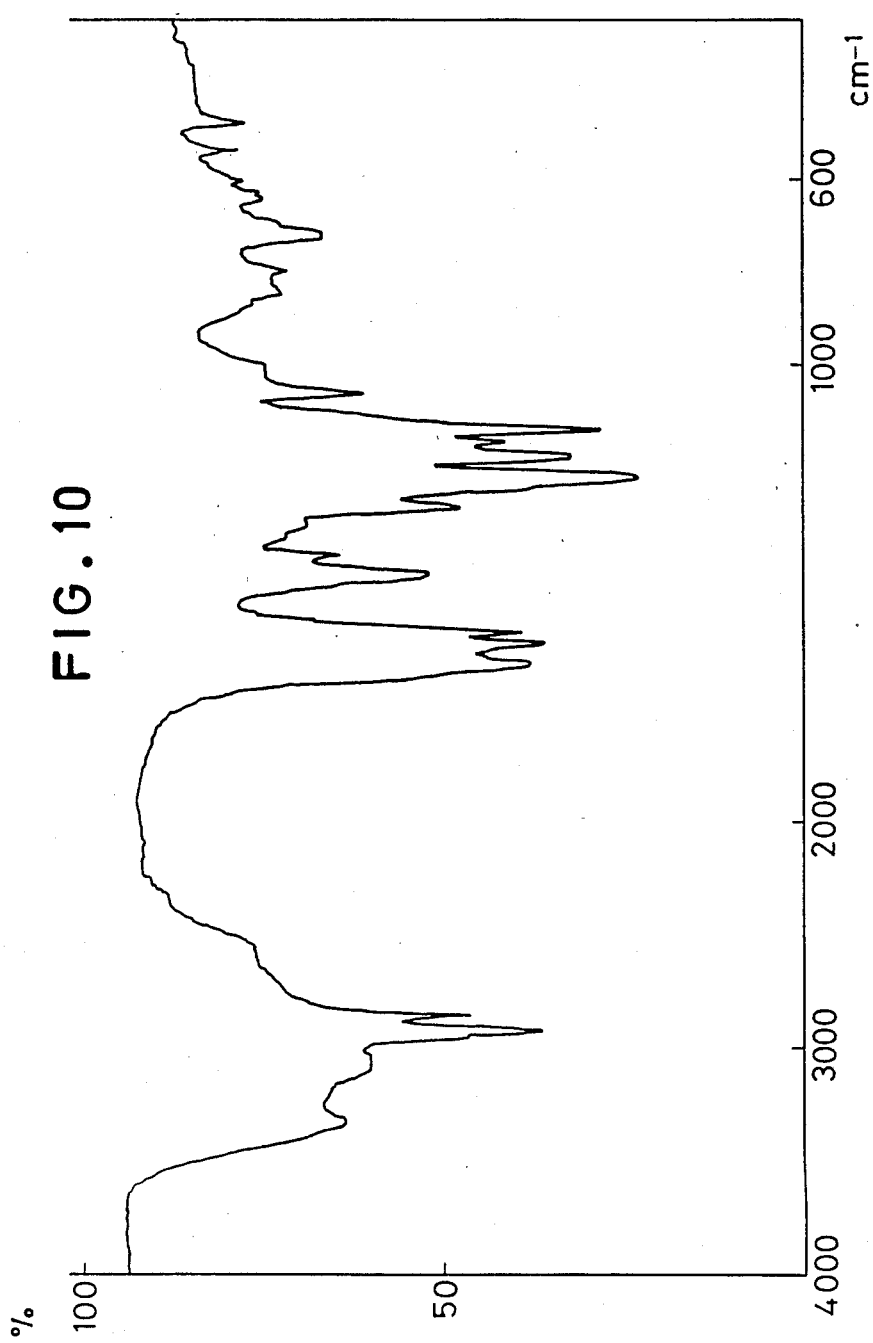
FIG. 10 is the infrared absorption spectrum of TPI-5.

(4) Molecular formula: $C_{36}H_{50}O_{13}$
(5) Molecular weight (FAB mass spectrum): 690
(6) Specific rotation:
$[\alpha]_D^{25} -19.6°$ (c=0.6, MeOH)
(7) Ultraviolet absorption spectrum: (FIG. 5)
in MeOH;
$\lambda_{max}$ (nm): 252 ($E^{1\%}$184), 310 (shoulder)
(8) Infrared absorption spectrum: (KBr) (FIG. 8)
3400, 2925, 2850, 1720, 1650, 1600, 1460, 1240, 1130, 1040 cm$^{-1}$.
(9) $^1$H-NMR spectrum (in deuterium methanol, 100 MHz):
δ(ppm): 0.88(t, 3H), 0.90(t, 3H), 1.31(m, 20H), 1.61(m, 4H), 2.08(s, 3H) 2.68(t, 2H), 2.94(t, 2H), 3.20-4.00(m, 3H), 4.00-4.60(m, 2H), 4.35(d, 1H), 6.44(d, 1H), 6.59(d, d, 2H), 6.73(d, 1H).
(10) $^{13}$C-NMR spectrum (in deuterium methanol, 25 MHz): 174.2(s), 173.1(s), 167.9(s), 164.4(s), 161.7(s), 158.3(s), 156.0(s), 149.2(s), 145.2(s), 116.5(d), 116.3(s), 113.3(s), 112.1(d), 109.4(d), 103.3(d), 103.0(d), 78.3(d), 75.8(d), 75.2(d), 71.8(d), 65.0(t), 37.2(t), 35.2(t), 33.3(t), 33.3(t), 33.3(t), 32.9(t), 31.1(t), 30.9(t), 30.6(t), 30.6(t), 24.0(t), 24.0(t), 21.0(q), 14.8(q) 14.8(q).
(11) Solubility:
Soluble; lower alcohol such as methanol, ethanol and butanol, ethyl acetate, dimethylsulfoxide, aqueous alkali.
Insoluble; hexane, benzene and petroleum ether.
(12) Color reaction:
Positive; potassium permanganate reaction, ferric chloride reaction, iodine reaction and Molisch reaction
Negative: ninhydrine reaction and iodoform reaction
(13) Thin layer chromatography: (Tokyo Kasei K.K. silica-gel f)

| (Developer) | (Rf) |
|---|---|
| chloroform - isopropanol - acetic acid: (10:4:0.1) | 0.54 |
| ethyl acetate - isopropanol - acetic acid: (10:4:0.1) | 0.51 |
| ethyl acetate - acetone - acetic acid: (6:6:0.1) | 0.35 |
| chloroform - methanol - acetic acid: (10:2:0.1) | 0.52 |

TPI-4
(1) Color and nature: white powder
(2) Nature: acidic substance
(3) Elementary analysis:

|  | C | H |
|---|---|---|
| found: | 62.35% | 7.57% |
| calculated: | 62.59% | 7.30% |

Figure 6:
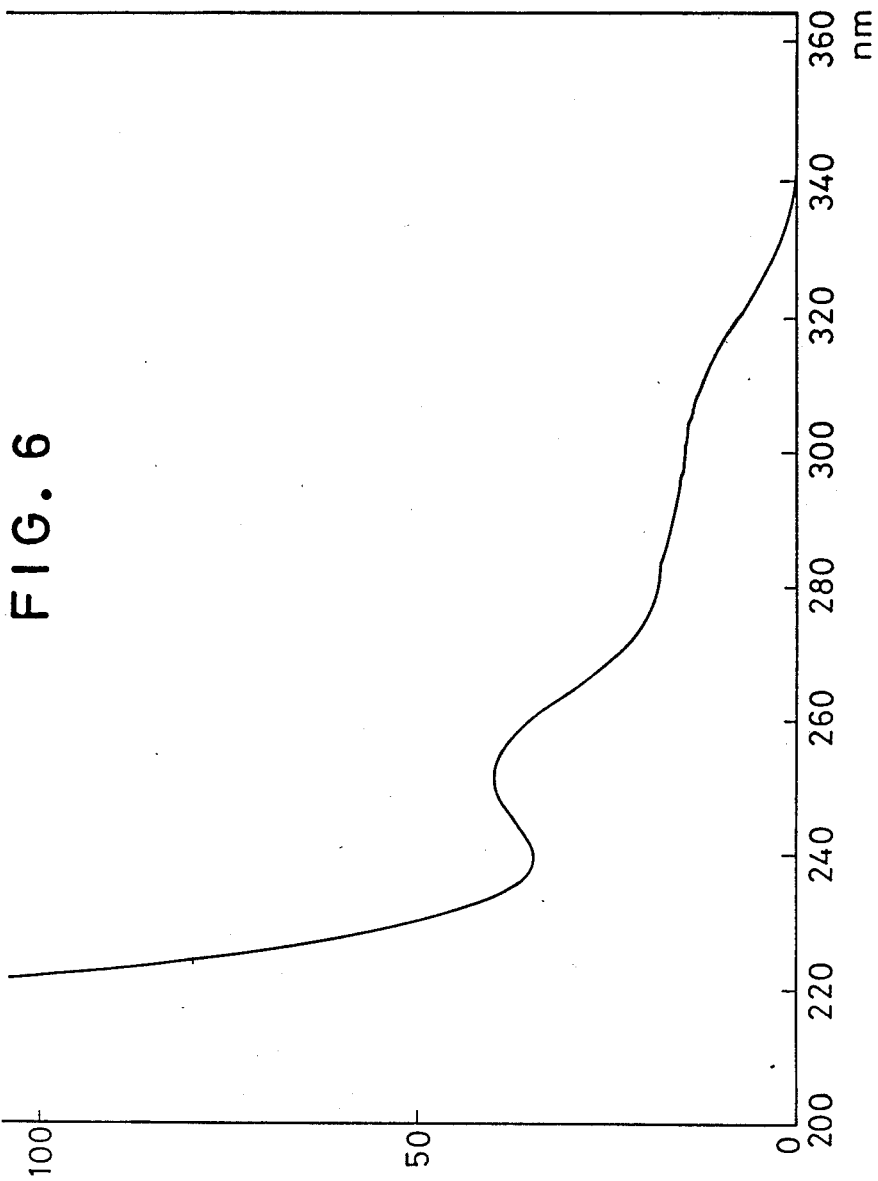
FIG. 6 is the ultraviolet absorption spectrum of TPI-4.

(4) Molecular formula: $C_{36}H_{50}O_{13}$
(5) Molecular weight (FAB mass spectrum): 690
(6) Specific rotation:
$[\alpha]_D^{25} -13.3°$ (c=0.4, MeOH)
(7) Ultraviolet absorption spectrum: (FIG. 6)
in MeOH;
$\lambda_{max}$ (nm): 252 ($E^{1\%}$172), 310 (shoulder)
(8) Infrared absorption spectrum: (KBr) (FIG. 8)
3420, 2930, 2860, 1730, 1660, 1610, 1470, 1240, 1140, 1040 cm$^{-1}$.
(9) $^1$H-NMR spectrum (in deuterium methanol, 100 MHz):
δ(ppm): 0.87(t, 3H), 0.90(t, 3H), 1.31(m, 20H), 1.61(m, 4H), 2.03(s, 3H) 2.68(t, 2H), 2.95(t, 2H), 3.20-4.00(m, 3H), 4.00-4.60(m, 2H), 4.87(d, 1H), 6.43(d, 1H), 6.60(d, d, 2H), 6.73(d, 1H).
(10) $^{13}$C-NMR spectrum (in deuterium methanol, 25 MHz): 174.2(s), 173.0(s), 168.0(s), 164.2(s), 161.8(s), 158.4(s), 156.0(s), 149.1(s), 145.2(s), 116.5(d), 116.1(s), 113.5(s), 111.9(d), 109.4(d), 103.7(d), 102.9(d), 75.2(d), 74.7(d), 72.5(d), 70.4(d), 64.9(t), 37.2(t), 35.2(t), 33.3(t), 33.3(t), 33.3(t), 33.0(t), 31.1(t), 31.0(t), 30.6(t), 30.6(t), 24.0(t), 24.0(t), 21.0(q), 14.8(q) 14.8(q).
(11) Solubility:
Soluble; lower alcohol such as methanol, ethanol and butanol, ethyl acetate, dimethylsulfoxide, aqueous alkali.
Insoluble; hexane, benzene and petroleum ether.
(12) Color reaction:
Positive; potassium permanganate reaction, ferric chloride reaction, iodine reaction and Molisch reaction
Negative; ninhydrine reaction and iodoform reaction
(13) Thin layer chromatography: (Tokyo Kasei K.K. silica-gel f)

| (Developer) | (Rf) |
|---|---|
| chloroform - isopropanol - acetic acid: (10:4:0.1) | 0.46 |
| ethyl acetate - isopropanol - acetic acid: (10:4:0.1) | 0.43 |
| ethyl acetate - acetone - acetic acid: (6:6:0.1) | 0.29 |
| chloroform - methanol - acetic acid: (10:2:0.1) | 0.48 |

TPI-5
(1) Color and nature: white powder
(2) Nature: acidic substance
(3) Elementary analysis:

|  | C | H |
|---|---|---|
| found: | 69.30% | 7.72% |
| calculated: | 69.11% | 7.87% |

Figure 7:
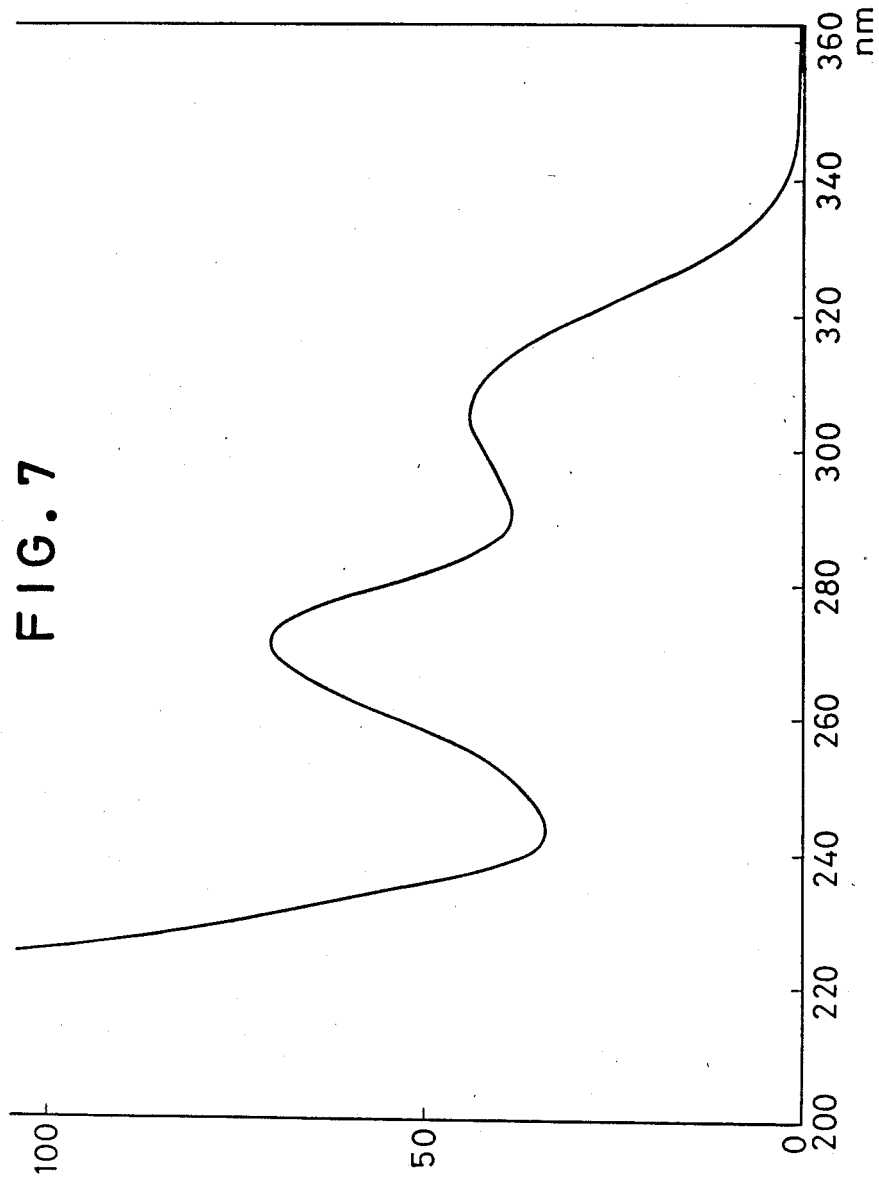
FIG. 7 is the ultraviolet absorption spectrum of TPI-5.

(4) Molecular formula: $C_{28}H_{38}O_7$
(5) Molecular weight: 486
(6) Ultraviolet absorption spectrum: (FIG. 7)

in MeOH;

$\lambda_{max}$ (nm): 271 ($E^{1\%} 389$) 305 ($E_{1\ cm}$ 243)

(7) Infrared absorption spectrum: (KBr) (FIG. 8) 3320, 2920, 2850, 1650, 1600, 1580, 1450, 1300, 1240, 1200, 1140, 1060 cm$^{-1}$.

(8) $^1$H-NMR spectrum (in deuterium methanol, 100 MHz):

δ(ppm): 0.85(t, 3H), 0.88(t, 3H), 1.27(m, 20H), 1.60(m, 4H), 3.02(t, t,) 6.32(S, 2H), 6.62(d, 1H), 6.74(d, 1H), 11.27(S, 1H).

(9) $^{13}$C-NMR spectrum (in deuterium methanol, 25 MHz): 174.7(s), 169.3(s), 166.3(s), 165.3(s), 161.4(s), 155.0(s), 150.0(s), 149.5(s), 116.2(d), 111.5(d), 109.0(d), 108.7(s), 104.2(s), 101.8(d), 37.3(t), 36.7(t), 32.3(t), 31.9(t), 31.9(t), 31.9(t), 29.9(t), 29.9(t), 29.3(t), 29.2(t), 22.8(t), 22.8(t), 14.2(q), 14.2(q).

(10) Solubility:

Soluble; lower alcohol such as methanol, ethanol and butanol, chloroform, ethyl acetate, dimethylsulfoxide, aqueous alkali.

Insoluble; hexane, benzene and petroleum ether.

(11) Color reaction:

Positive; potassium permanganate reaction, ferric chloride reaction, iodine reaction and Molisch reaction Negative; ninhydrine reaction and iodoform reaction

(12) Thin layer chromatography: (Tokyo Kasei K.K. silica-gel f)

| (Developer) | (Rf) |
|---|---|
| chloroform - isopropanol - acetic acid: (10:4:0.1) | 0.87 |
| ethyl acetate - isopropanol - acetic acid: (10:4:0.1) | 0.68 |
| ethyl acetate - acetone - acetic acid: (6:6:0.1) | 0.78 |
| chloroform - methanol - acetic acid: (10:2:0.1) | 0.77 |

According to the above physico-chemical properties, TPI-1, TPI-2, TPI-3, TPI-4 and TPI-5 have the chemical structure illustrated in formula (I).

TPI of the present invention is a novel substance completely different from prior known PDE inhibitors produced by microorganisms. Among the known PDE inhibitors, PDE-I, PDE-II, CC-1065, APD-I, APD-II and APD-III are nitrogenous substances and reticulol and terferol are compounds of molecular formula $C_{11}H_{10}O_5$ and $C_{19}H_{16}O_5$, respectively, all of which are different from the present TPI.

TPI of the present invention has strong PDE inhibitory activity. The bovine heart PDE inhibitory action of the TPI is illustrated hereinbelow.

Method 40 mM Tris-HCl buffer solution (pH 7.5), 2 mM magnesium chloride, 0.4 mM c-AMP, PDE (30 μg protein, Boehringer Mannheim Co.) and TPI are combined to form a reaction mixture (1.0 ml) and the same is incubated at 30° C. for 30 minutes. The reaction is stopped by adding 55% trichloroacetic acid (0.1 ml) and the produced 5'-AMP is measured by HPLC (Hitachi, 655 system) (column: Hitachi #3056, 4×150 mm, migration layer: 10 mM KH$_2$PO$_4$ (pH 2.0)-MeOH (10:1), migration speed: 1.5 ml/min. detector: 262 mμ). The inhibition ratio is calculated by the following equation:

Inhibition ratio = (A−B)/A × 100 (%)

wherein

A: amount of 5'-AMP without TPI

B: amount of 5'-AMP with TPI

IC$_{50}$, a concentration of TPI at an inhibition ratio 50%, is shown in the following:

Results

| Compound | IC$_{50}$ concentration (μg/ml) |
|---|---|
| TPI-1 | 2.8 |
| TPI-2 | 5.4 |
| TPI-3 | 2.8 |
| TPI-4 | 3.5 |
| TPI-5 | 2.3 |
| Papaverine | 25 |
| Nicardipine | 6.0 |
| Teophyllin | 470 |

No deaths occurred when TPI-1 100 mg/kg was injected intraperitoneally in mice.

As illustrated hereinabove, TPI of the present invention has strong inhibitory activity against PDE and low toxicity, and hence is useful as a bronchodilator, cardiac activity regulator, smooth muscle relaxant and hormone excretion stimulant.

The following examples illustrate the present invention but are not to be construed as limiting the scope of the invention.

EXAMPLE 1

One loopful of the strain of Nodulisporium sp. M5220 FERM P-8133 was inoculated into a medium (pH 6.5, 100 ml, sterilized at 120° C. for 20 min.) containing glucose 2%, peptone 1%, CSL 1%, potassium dihydrogen phosphate 0.2%, magnesium sulfate 0.1% and Celite 1% in a 500 ml Erlenmeyer flask, and the material was cultured at 26° C. for 4 days to prepare a seed culture. The seed culture was inoculated at 3% volume ratio, into a medium (pH 7.0, 100×100 ml) consisting of glucose 5%, pharma media 2%, CSL 0.5%, potassium monohydrogen phosphate 0.1%, magnesium sulphate 0.2%, calcium carbonate 0.5%, ferrous sulfate 0.0005%, zinc sulfate 0.0002%, cobalt chloride 0.0001%, manganese sulfate 0.0003% and copper sulfate 0.0002%. The fermentation was carried out at 26° C. for 5 days in a rotary shaker. The cultured broth (10 lit.) was centrifuged to obtain a supernatant solution (8.5 lit.) Ethyl acetate (5 lit.) was added to the supernatant, the pH was adjusted to pH 2 by adding dropwise 2N HCl, and the obtained ethyl acetate layer (4.5 lit.) was separated. Water (3 lit.) was added to the ethyl acetate layer and the pH was adjusted to pH 9 by adding conc. aqueous ammonia to transfer the TPI into the aqueous layer. Ethyl acetate (2 lit.) was added to the aqueous layer (3 lit.), and the pH was adjusted to 2 by adding 2N HCl with stirring to obtain an ethyl acetate layer (approx. 2 lit.) The ethyl acetate layer was dried by adding anhydrous sodium sulfate and concentrated in vacuo to obtain a brownish powder (approx. 6 g).

EXAMPLE 2

Crude TPI powder (6 g) obtained in Example 1 dissolved in methanol (30 ml) was mixed with silica-gel powder (4 g), and the mixture was stirred and concentrated in vacuo to remove the methanol. The mixture was layered onto the top of a silica-gel column (400 ml) previously packed with a mixed solution of chloroform-isopropanol-acetic acid (10:2:0.1) and eluted with the same solvent mixture. Each 20 g fraction was checked by TLC developed with chloroform-isopropanol-acetic acid (10:4:0.1). The spots showing Rf=0.54, Rf=0.46, Rf=0.25 and Rf=0.19 detected by ultraviolet absorption using a Manasule lamp (trade name) or a decoloration reaction with potassium permanganate, were fractionated. Fractions Nos. 13-28 contained TPI-3 (Rf=0.54) and TPI-4 (Rf=0.46), fractions Nos. 71-122 contained TPI-1 (Rf=0.25) and fractions Nos. 123-187 contained TPI-1 (Rf=0.25) and TPI-2 (Rf=0.19).

Fractions Nos. 13-28 were collected, concentrated in vacuo to 20 ml, charged on a column of silica gel (200 ml) previously packed with a mixture of ethyl acetate-acetone-acetic acid (10:6:0.1) and eluted with the same solvent. The eluate was collected in 20 g fractions, tested by silica gel TLC developed with a mixture of ethyl acetate-acetone-acetic acid (6:6:0.1), and the fractions were collected containing spots corresponding to Rf=0.35 and Rf=0.29. Fractions Nos. 35-40 containing a substance corresponding to Rf=0.35 were collected and concentrated in vacuo to approximately 3 ml. n-Hexane was added to the residue to precipitate a substance containing TPI-3, which was washed with n-hexane and dried in vacuo to obtain TPI-3 (20 mg).

Fractions Nos. 48-69 containing a substance corresponding to Rf=0.29 were collected and concentrated in vacuo to approximately 3 ml. n-Hexane was added to the residue to precipitate a substance containing TPI-4, which was washed with n-hexane and dried in vacuo to obtain TPI-4 (15 mg).

EXAMPLE 3

Fractions Nos. 71-122 containing TPI-1 showing Rf=0.25 were collected and concentrated to 20 ml in vacuo. Ethyl acetate was added thereto, to 200 ml. Further water (200 ml) was added and the mixture was vigorously stirred. The ethyl acetate layer was concentrated in vacuo to approximately 10 ml. n-Hexane was added therein to precipitate TPI-1. The precipitate was placed on the glass filter, washed with n-hexane and concentrated in vacuo to obtain purified TPI-1 (1.8 g).

Fractions Nos. 123-187 containing TPI-1 (Rf=0.25) and TPI-2 (Rf=0.19) obtained in Example 2 were collected and concentrated in vacuo. The residue dissolved in methanol (20 ml) was mixed well with silica gel powder (2 g). After removing the methanol in vacuo, the mixture was charged on a column of silica gel (200 ml) previously packed with chloroform-methanol-acetic acid (10:2:0.1) and eluted with the same solvent mixture. Each fraction (20 g) was checked by silica gel TLC developed with chloroform-isopropanol-acetic acid (10:4:0.1) and the spot was detected by ultraviolet absorption using a Manasule lamp and the decoloring reaction of potassium permanganate. Fractions Nos. 54-130 containing only a substance showing Rf=0.19 were collected, concentrated in vacuo to 20 ml, and ethyl acetate (200 ml) and water (200 ml) were added thereto and the mixture was vigorously stirred. The ethyl acetate was separated, concentrated in vacuo to 10 ml and n-hexane was added thereto to precipitate TPI-2, which was washed with n-hexane and then dried in vacuo to obtain TPI-2 (600 mg).

EXAMPLE 4

TPI-1 (50 mg) obtained in Example 3 was dissolved in 0.1M phosphate buffer (pH 6.5, 4 ml), and β-glucosidase (Sigma Co., 4.5 U/mg, 4 mg) was added thereto. The mixture was incubated at 26° C. for 7 days, whereby approximately 50% of the TPI-1 was transformed to TPI-5. The reaction mixture was adjusted to pH 3 with anhydrous sodium sulfate and concentrated in vacuo. The residue was charged on a column of silica gel (28 ml) previously packed with a mixture of chloroform-methanol-acetic acid (20:1:0.1) and eluted with the same mixture. The eluate of 5 g fractions was collected and fractions Nos. 28-31 were concentrated and washed with n-hexane and dried in vacuo to obtain white powdery TPI-5 (15 mg).

What is claimed is:

1. A compound of the formula

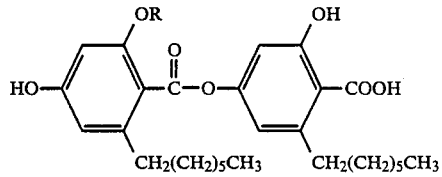

wherein R is β-D-glucopyranosyl, β-D-galactopyranosyl, 6'-O-acetyl-β-D-glucopyranosyl or 6'-O-acetyl-β-D-galactopyranosyl, or a pharmacologically acceptable salt thereof.

2. A process for the production of a compound of the formula

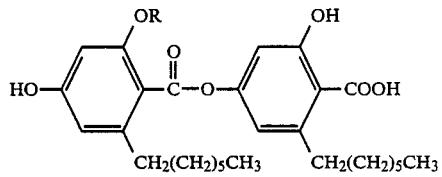

wherein R is β-D-glucopyranosyl, β-D-galactopyranosyl, 6'-O-acetyl-β-D-glucopyranosyl, or 6'-O-acetyl-β-D-galactopyranosyl, which comprises culturing a microorganism belonging to the genus Nodulisporium and adapted to produce said compound in a culture medium, and isolating the produced said compound from the cultured medium.

3. A process as claimed in claim 2, and converting the thus-isolated compound to a pharmaceutically acceptable salt.

4. A process according to claim 2, wherein said microorganism is Nodulisporium sp. M5220 FERM P-8133.

* * * * *